United States Patent
Park et al.

(10) Patent No.: US 10,328,171 B2
(45) Date of Patent: Jun. 25, 2019

(54) AIR FRESHENER DEVICE FOR VEHICLE

(71) Applicants: HYUNDAI MOTOR COMPANY, Seoul (KR); Kia Motors Corporation, Seoul (KR); Hanon Systems, Daejeon (KR)

(72) Inventors: June Kyu Park, Hwaseong-si (KR); Kwang Woon Cho, Yongin-si (KR); Yong Jun Jee, Daejeon (KR); Jae Ho Kim, Daejeon (KR)

(73) Assignees: Hyundai Motor Company, Seoul (KR); Kia Motors Corporation, Seoul (KR); Hanon Systems, Daejeon (KR)

( * ) Notice: Subject to any disclaimer, the term of this patent is extended or adjusted under 35 U.S.C. 154(b) by 0 days.

(21) Appl. No.: 14/621,038

(22) Filed: Feb. 12, 2015

(65) Prior Publication Data

US 2016/0101669 A1    Apr. 14, 2016

(30) Foreign Application Priority Data

Oct. 13, 2014    (KR) .................. 10-2014-0137409

(51) Int. Cl.
*B60H 3/00* (2006.01)
*A61L 9/12* (2006.01)

(52) U.S. Cl.
CPC ............. *A61L 9/12* (2013.01); *A61L 9/127* (2013.01); *B60H 3/0021* (2013.01); *B60H 2003/0042* (2013.01)

(58) Field of Classification Search
CPC .............. B60H 3/00; F24F 13/00; A61L 9/12
USPC ....................................................... 454/156
See application file for complete search history.

(56) References Cited

U.S. PATENT DOCUMENTS

| | | | | |
|---|---|---|---|---|
| 4,696,844 A | * | 9/1987 | Spector | A61L 9/042 428/46 |
| 5,304,358 A | * | 4/1994 | Hoyt | A61L 9/12 239/56 |
| 5,350,444 A | * | 9/1994 | Gould | B60H 3/0641 454/158 |
| 5,417,743 A | * | 5/1995 | Dauber | B01D 46/10 360/99.15 |
| 5,869,009 A | * | 2/1999 | Bellefeuille | B01D 53/04 422/171 |

(Continued)

FOREIGN PATENT DOCUMENTS

| | | | |
|---|---|---|---|
| JP | 2005238655 A | * | 9/2005 |
| JP | 2006-081618 A | | 3/2006 |

(Continued)

OTHER PUBLICATIONS

Korean Office Action dated Oct. 8, 2015 issued in Korean Patent Application No. 10-2014-0137409.

(Continued)

*Primary Examiner* — Steven B McAllister
*Assistant Examiner* — Samantha Miller
(74) *Attorney, Agent, or Firm* — Morgan, Lewis & Bockius LLP

(57) ABSTRACT

An air freshener for a vehicle includes a housing having an air inlet and an air outlet at both ends thereof. A perfume container is provided inside the housing, in which a plurality of aromatics having different physical states are laminated. An aromatics laminated at an uppermost layer is evaporated by air passing through an interior of the housing.

11 Claims, 5 Drawing Sheets

(56) References Cited

U.S. PATENT DOCUMENTS

| | | | | |
|---|---|---|---|---|
| 6,554,887 B1* | 4/2003 | Inglis | A01M 1/14 | 206/484.1 |
| 6,878,057 B1* | 4/2005 | Calloura | A61L 9/12 | 422/123 |
| 7,306,659 B2* | 12/2007 | Gorton | B01D 46/0032 | 360/97.17 |
| 7,611,557 B2* | 11/2009 | Hoffman | G11B 33/1486 | 219/735 |
| 7,934,387 B2* | 5/2011 | Lee | B01D 46/0023 | 422/120 |
| 7,976,606 B1* | 7/2011 | Nicholson | B01D 46/10 | 55/385.1 |
| 8,776,832 B2* | 7/2014 | Tuma | G11B 33/1466 | 137/549 |
| 2002/0198117 A1* | 12/2002 | Dente | A61L 9/04 | 510/101 |
| 2004/0003724 A1* | 1/2004 | Ellis | A01M 1/205 | 96/115 |
| 2005/0011883 A1* | 1/2005 | Clothier | F28D 20/0056 | 219/618 |
| 2006/0210421 A1* | 9/2006 | Hammond | A61L 9/03 | 422/3 |
| 2007/0178821 A1* | 8/2007 | Zimmerman | B60H 3/0007 | 454/69 |
| 2008/0009560 A1* | 1/2008 | McKay, Jr. | A61L 9/042 | 523/102 |
| 2008/0011871 A1* | 1/2008 | Sexton | A01M 1/2044 | 239/55 |
| 2008/0016743 A1* | 1/2008 | Graves | A47G 1/0616 | 40/768 |
| 2008/0064319 A1* | 3/2008 | Chezick | F24F 13/085 | 454/341 |
| 2008/0179424 A1* | 7/2008 | Cheung | A61L 9/03 | 239/60 |
| 2009/0209190 A1* | 8/2009 | Gould | B01D 39/1623 | 454/158 |
| 2009/0230210 A1* | 9/2009 | Wang | A61L 9/042 | 239/53 |
| 2009/0298413 A1* | 12/2009 | Arold | B01D 46/0005 | 454/158 |
| 2010/0015904 A1* | 1/2010 | Yeh | B01D 46/0005 | 454/184 |
| 2010/0019059 A1* | 1/2010 | Bulsink | A61L 9/127 | 239/55 |
| 2010/0314461 A1* | 12/2010 | Gruenbacher | A61L 9/12 | 239/6 |
| 2011/0196325 A1* | 8/2011 | Isele | A61F 13/4942 | 604/365 |
| 2013/0164178 A1* | 6/2013 | Carmichael | A61L 9/12 | 422/123 |
| 2014/0158789 A1* | 6/2014 | Haymond | A61L 9/12 | 239/34 |
| 2014/0193295 A1* | 7/2014 | Fischer | A61L 9/12 | 422/4 |

FOREIGN PATENT DOCUMENTS

| | | |
|---|---|---|
| KR | 10-2004-0036319 A | 4/2004 |
| KR | 10-2009-0050553 A | 5/2009 |
| KR | 10-2010-0093724 A | 8/2010 |
| KR | 10-2011-0075269 A | 7/2011 |
| KR | 10-2012-0128186 A | 11/2012 |
| KR | 10-2014-0086891 A | 7/2014 |

OTHER PUBLICATIONS

Notice of Allowance issued in Korean Application No. 10-2014-0137409 dated Mar. 28, 2016.

\* cited by examiner

AIR FRESHENER DEVICE FOR VEHICLE

CROSS-REFERENCE(S) TO RELATED APPLICATION

The present application claims the benefit of priority to Korean Patent Application Number 10-2014-0137409 filed on Oct. 13, 2014, the entire contents of which application are incorporated herein for all purposes by this reference.

TECHNICAL FIELD

The present disclosure relates to an air freshener device for a vehicle, and more particularly, to an air freshener device for a vehicle in which a lifespan of aromatics can be lengthened and a perfume with constant intensity can be produced even after a predetermined time is lapsed.

BACKGROUND

Recently, an air freshener for a vehicle has been widely provided for purifying air inside the vehicle since various harmful substances, such as dust or smoke gas produced when operating a heater or an air conditioner while the vehicle travels, are introduced into the vehicle, or bacterial foreign substance such as mold produced inside the air conditioner is introduced into the vehicle as an air conditioner is operated. Lifespan and performance of the air freshener may be determined according to aromatics contained in the air freshener.

For example, a crude liquid of perfume is diluted in a vessel, and then, the perfume liquid naturally evaporates and emits fragrance, but storing the crude liquid is unsanitary and not easy. Further, the fragrance smells strong only when the perfume is injected, and the perfume intensity is not uniform.

As another way for implementing an air freshener in a case where a perfume liquid is absorbed into gauze, and then, the perfume liquid may be evaporated or injected into inside a vehicle using a separate air blower. In this case, the air freshener can be easily manufactured, but a lifespan of the perfume is shortened, and thus, frequent refill of the perfume crude liquid is necessary.

Further, when the perfume liquid is prepared as a gel state (colloid liquid is hardened to jelly type) and naturally evaporates as another method for implementing an air freshener, the gel type is worn out after a predetermined time is elapsed, and the lifespan of the perfume may be shortened.

As still further way for implementing an air freshener in a case where aromatics may be prepared as a ball type, however, in this case the perfume intensity is not uniform, and thus, the lifespan of air freshener can be shortened. Additionally, a large amount of perfume material is wasted when preparing the aromatics, and thus, the amount of the perfume decreases.

In addition, in a case where the perfume liquid is prepared as a solid state (colloid liquid is solidified) and then evaporated naturally. In this case, since an air freshener is prepared as a solid type, a shape thereof does not change, however, a lifespan of the perfume is shortened.

As described above, in case where one type of perfume material is used as aromatics, a lifespan of perfume is extremely limited, and a shape of evaporated perfume is changed or diluted after a predetermined time elapses.

The description provided above as a related art of the present invention is just for helping in understanding the background of the present invention and should not be construed as being included in the related art known by those skilled in the art.

SUMMARY

The present disclosure has been proposed to solve the above drawbacks, and an aspect of the present inventive concept provides an air freshener device for a vehicle in which a lifespan of aromatics can be lengthened and a perfume with constant intensity can be produced even though a predetermined time is lapsed comparing to initial perfume intensity.

According to an exemplary embodiment of the present inventive concept, an air freshener device for a vehicle includes a housing having an air inlet and an air outlet at both ends of the housing. A perfume container is provided inside the housing, in which a plurality of aromatics having different physical states are laminated. An aromatics laminated at an uppermost layer is evaporated by air passing through an interior of the housing.

The perfume container may include a first aromatics laminated on the uppermost layer and a second aromatics having one surface laminated on the first aromatics and the opposite surface seated on an inner surface of the housing. The second aromatics has a lifespan longer than that of the first aromatics in its physical state.

The first aromatics may be in a gel state and the second aromatics may be in a solid state.

A porous filter may be provided between the first aromatics and the second aromatics.

An aromatics housing member may be provided in which the the first aromatics is housed.

The aromatics housing member may be made of a porous material and may be laminated on the one surface of the second aromatics.

A reception portion may be provided on an inner surface of the housing, which surrounds edges of the second aromatics.

Air may be introduced into the air inlet by an air blower of an air conditioner and the air outlet is connected to the interior of the vehicle.

The description provided above as a related art of the present disclosure is just for helping in understanding the background of the present disclosure and should not be construed as being included in the related art known by those skilled in the art.

BRIEF DESCRIPTION OF THE DRAWINGS

The above and other features of the present inventive concept will now be described in detail with reference to exemplary embodiments thereof illustrating the accompanying drawings which are given herein below by way of illustration only, and thus are not limitative of the present disclosure.

Figure 1:
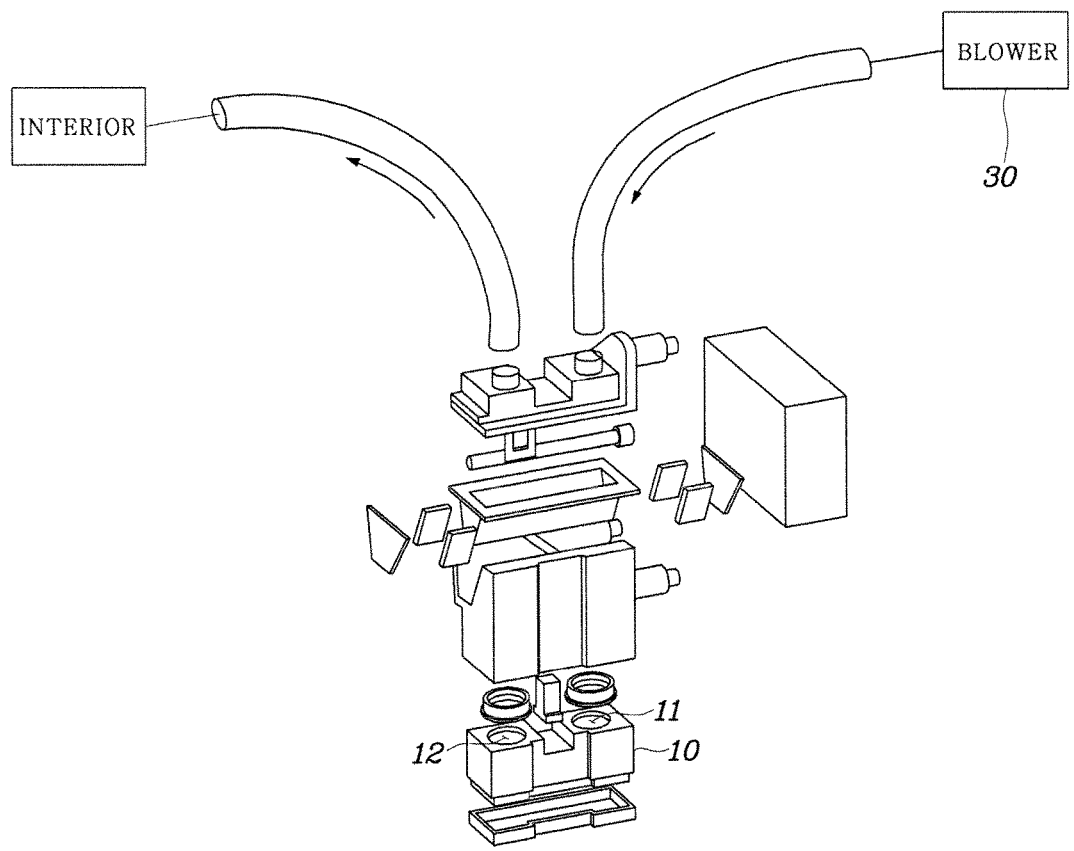
FIG. 1 is a view illustrating schematically an air freshener device for a vehicle according to an embodiment of the present inventive concept.

It should be understood that the appended drawings are not necessarily to scale, presenting a somewhat simplified representation of various features of the present disclosure as disclosed herein, including, for example, specific dimensions, orientations, locations, and shapes will be determined in part by the particular intended application and use environment.

In the figures, reference numbers refer to the same or equivalent parts of the present disclosure throughout the several figures of the drawing.

DETAILED DESCRIPTION

Hereinafter reference will now be made in detail to various embodiments of the present inventive concept, examples of which are illustrated in the accompanying drawings and described below. While the inventive concept will be described in conjunction with exemplary embodiments, it will be understood that present description is not intended to limit the inventive concept to those exemplary embodiments. On the contrary, the inventive concept is intended to cover not only the exemplary embodiments, but also various alternatives, modifications, equivalents and other embodiments, which may be included within the spirit and scope of the invention as defined by the appended claims.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Hereinafter, fuel cells according to exemplary embodiments of the present inventive concept will be described with reference to the accompanying drawings.

An air freshener device for a vehicle may include mainly a housing 10 and a perfume element 20.

Referring to FIGS. 2 to 5, the housing 10 has an air inlet 11 that is formed at one upper end of the housing 10 and an air outlet 12 that is formed at another upper end of the housing 10 so that the air introduced from the air inlet 11 passes through an interior of the housing 10 and is discharged to the air outlet 12.

The perfume element 20 is provided inside the housing 10, in which a plurality of aromatics having different physical states are laminated and an aromatics that are laminated at an uppermost layer is evaporated by air passing through the housing 10.

That is, fragrance of the aromatic laminated at the uppermost layer is discharged while the aromatics laminated at the uppermost layer is evaporated by the air passing through the housing 10 among the plurality of aromatics having different physical sates, and the right lower layer of the aromatics is evaporated and the fragrance is discharged after the aromatics at the uppermost layer is exhausted. Accordingly, perfume producing time is increased to increase a lifespan of the air freshener device.

Figure 2:
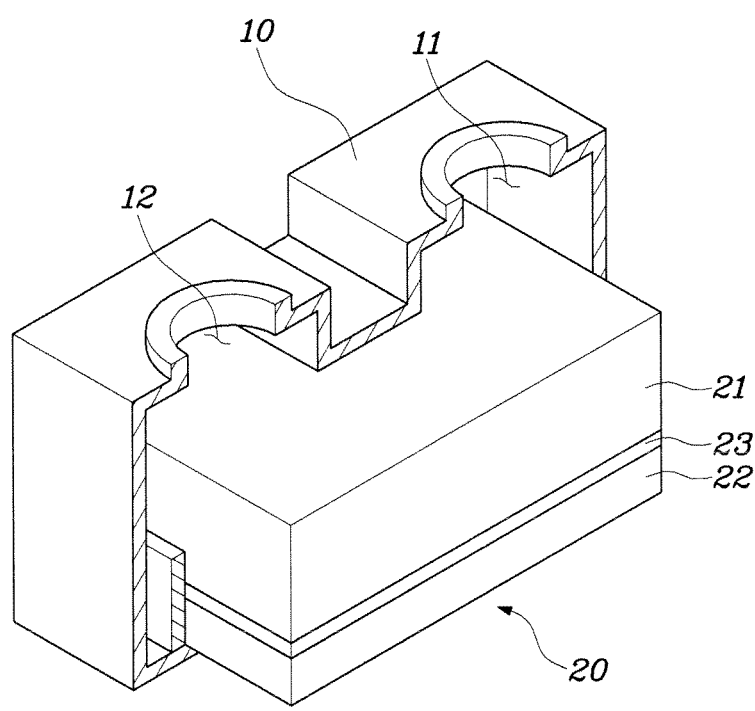
FIG. 2 is a view illustrating schematically an air freshener device for a vehicle in which a perfume container is embedded in a housing according to an embodiment of the present inventive concept.
Figure 3:
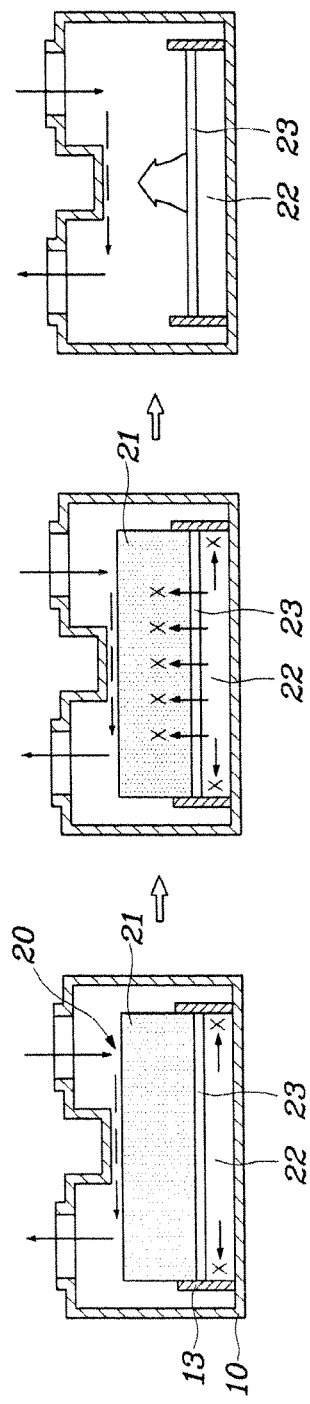
FIG. 3 is a view illustrating evaporation of a first aromatics and second aromatics in the perfume container as shown in FIG. 2.

Referring to FIGS. 2 and 3, the perfume element 20 may include a first aromatics 21 and a second aromatics 22.

For example, the first aromatics 21 is provided at the uppermost layer of the perfume element 20 and a bottom surface of the first aromatics 21 is laminated on an upper surface of the second aromatics 22, and a bottom surface of the second aromatics 22 is seated on a floor of the housing 10. Further, a reception portion 13 may be provided on a lower surface of the housing 10, which surrounds edges of the second aromatics 22.

That is, fragrance of the first aromatics 21 is diffused firstly by the air passing through the housing 10, and then, fragrance of the second aromatics 22 is diffused and discharged.

Here, the second aromatics 22 may have a longer lifespan than that of the first aromatics 21 in its physical state. The first aromatics 21 may be in a gel state of perfume liquid, and the second aromatics 22 is in a solid state of perfume liquid.

Especially, a porous filter 23 may be provided between the first aromatics 21 and the second aromatics 22. For example, the porous filter 23 may be a membrane having fine holes, through which liquid phase is not permissible but evaporated perfume is permissible.

That is, only the perfume diffused from the second aromatics 22 passes through the porous filer 23 and is discharged after all perfume of the first aromatics 21 in the gel sate is exhausted, thereby greatly increasing a lifespan of the aromatics.

Figure 4:
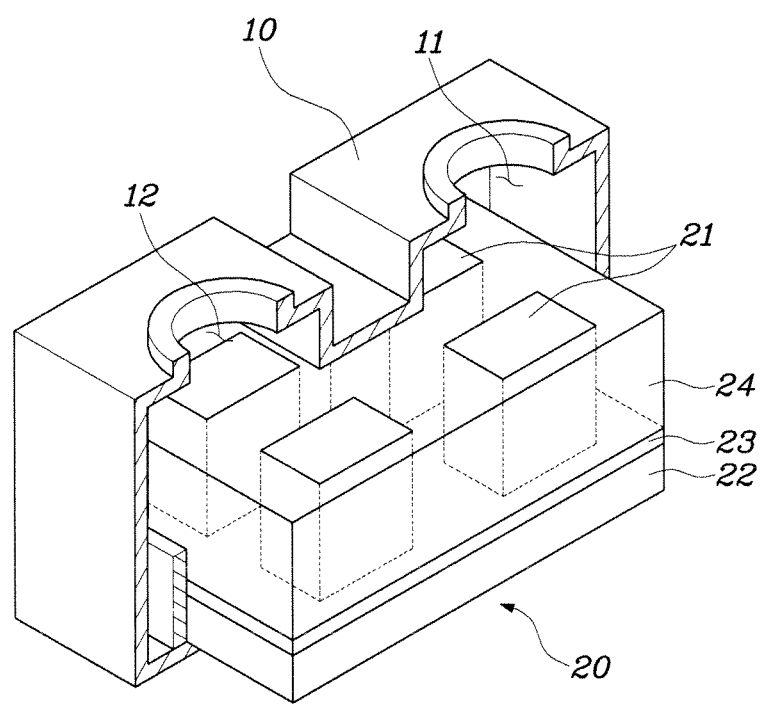
FIG. 4 is a view illustrating an air freshener device for a vehicle in which a first aromatics is housed in an aromatics housing member according to another embodiment of the present inventive concept.
Figure 5:
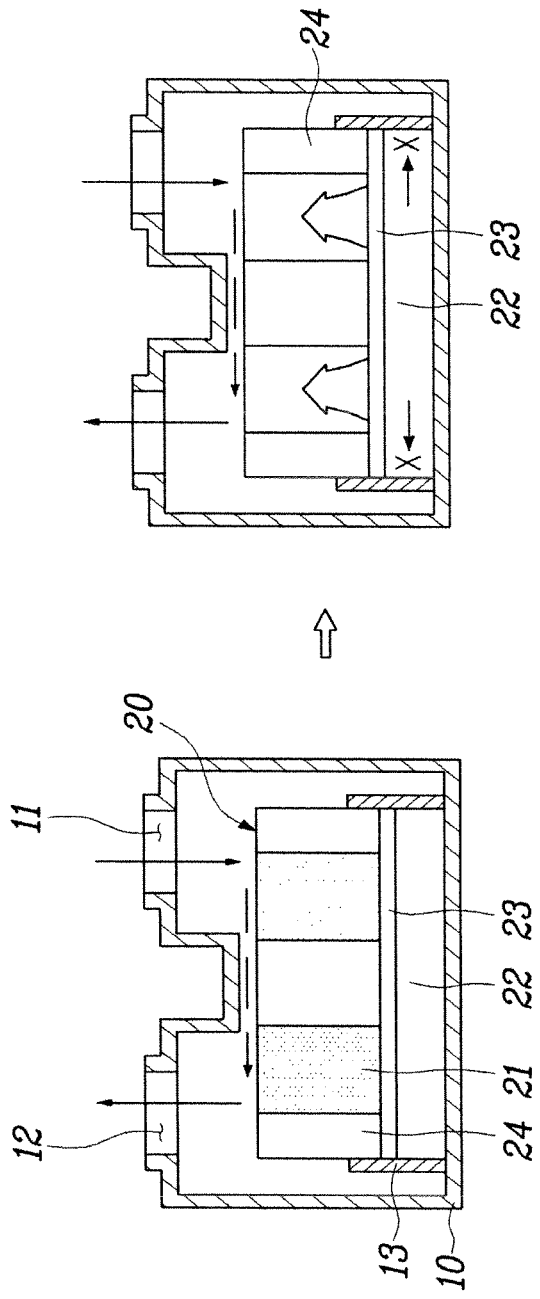
FIG. 5 is a view illustrating evaporation of a first aromatics and second aromatics in the perfume container as shown in FIG. 4.

Referring to FIGS. 4 and 5, an aromatics housing member 24 may be provided and surrounds the first aromatics 21.

For example, the aromatics hosing member 24 has at least one hole formed along a length direction, into which the first aromatics 21 is inserted. Thus, the bottom surface of the first aromatics 21 is laminated on the upper surface of the second aromatics 22, and only the upper surface of the first aromatics 21 is exposed to the air passing through housing 10.

Accordingly, an evaporation surface area of the first aromatics 21 is minimized to further increase the lifespan of the aromatics.

Further, the aromatics housing member 24 may be made of porous material and connected to the porous filter 23 laminated on one surface of the second aromatics 22.

For example, the aromatics housing member 24 is made of ceramic porous material having a porous surface area of nano size, and thus, the aromatics can be filled in the aromatics housing member 24.

Accordingly, storing capacity of the aromatics is increased to maintain the fragrance of the aromatics for a long time, and the second aromatics 22 is immersed in the aromatics housing member 24 after the first aromatics 21 is discharged, thereby continuously supplying the fragrance. Therefore, the lifespan of the air freshener device can be increased to prevent frequent refill of the aromatics and maintain the fragrance after a predetermined time is lapsed thereby improving marketability.

As shown in FIG. 1, the air inlet 11 is connected to a blower 30 of the air conditioner and air is introduced therein through the air blower 30, and the air outlet 12 is connected to an interior of a vehicle such that the perfume diffused from the perfume element 20 and air introduced from the air inlet 11 are discharged through the air outlet 12. Accordingly, while the air conditioner of a vehicle is operated, the perfume diffused from the perfume element 20 is introduced into the interior of the vehicle and supplies fragrance to the inside of the vehicle.

At this time, the air freshener of the present disclosure may be installed on a side of the air conditioner or on an inside of a globe box so that the perfume element 20 can be refilled easily.

According to the present disclosure, only the perfume diffused from the second aromatics is discharged through a porous filter after the first aromatics in a gel state is discharged all, thereby increasing a lifespan of the aromatics.

Further, an evaporation surface area of the first aromatics is minimized and a storing capacity of the aromatics is increased, thereby maintaining fragrance of the aromatics for a long time, and the second aromatics is immersed in the aromatics housing member after the first aromatics is discharged. Thereby continuously supplying the fragrance even after a predetermined time is lapsed, thus improving marketability.

The inventive concept has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. An air freshener device for a vehicle, comprising:
   a housing having an air inlet formed at one end of the housing and an air outlet formed at another end of the housing; and
   a perfume element provided inside the housing, in which the perfume element having layers of a plurality of aromatics having different physical states and laminated,
   wherein the perfume element comprises:
      a first aromatics laminated on an uppermost layer of the perfume element, which is evaporated by air passing through an interior of the housing;
      a second aromatics having a lifespan longer than that of the first aromatics in its physical state; and
      a porous filter disposed between the first aromatics and the second aromatics,
   wherein the first aromatics is in a gel state and the second aromatics is in a solid state, and
   wherein the porous filter is laminated on one surface of the second aromatics, and the opposite surface of the second aromatics is seated on an inner surface of the housing.

2. The air freshener device of claim 1, wherein an aromatics housing member is provided in which the first aromatics is accommodated.

3. The air freshener device of claim 2, wherein the aromatics housing member is made of a porous material and is connected to the porous filter.

4. The air freshener device of claim 3, wherein the aromatics housing member is made of a ceramic porous material which has a porous surface area.

5. The air freshener device of claim 2, wherein the aromatics housing member has at least one hole formed along a length direction thereof, into which the first aromatics is inserted.

6. The air freshener device of claim 5, wherein an upper surface of the first aromatics in the aromatics housing member is exposed to the air passing through the interior of the housing.

7. The air freshener device of claim 1, wherein a reception portion is provided on the inner surface of the housing, which surrounds edges of the second aromatics.

8. The air freshener device of claim 1, wherein air is introduced into the air inlet by an air blower of an air conditioner and the air outlet is connected to an interior of the vehicle.

9. The air freshener device of claim 8, wherein the air introduced from the air inlet is discharged to the air outlet.

10. The air freshener device of claim 1, wherein the porous filter is a membrane having fine holes, through which only an evaporated perfume is permissible.

11. The air freshener device of claim 1, wherein one surface of the first aromatics is connected to the porous filter laminated on the second aromatics.

* * * * *